US010514485B2

(12) United States Patent
Kostuk et al.

(10) Patent No.: US 10,514,485 B2
(45) Date of Patent: Dec. 24, 2019

(54) HOLOGRAPHIC DIFFRACTION-THROUGH-APERTURE SPECTRUM SPLITTING SYSTEM AND METHOD

(71) Applicant: The Arizona Board of Regents on behalf of The University of Arizona, Tucson, AZ (US)

(72) Inventors: Raymond K. Kostuk, Tucson, AZ (US); Shelby D. Vorndran, Tucson, AZ (US); Deming Zhang, Gilbert, AZ (US); Juan Manuel Russo, Tucson, AZ (US); Michael Gordon, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 239 days.

(21) Appl. No.: 14/072,443

(22) Filed: Nov. 5, 2013

(65) Prior Publication Data

US 2014/0130843 A1 May 15, 2014

Related U.S. Application Data

(60) Provisional application No. 61/796,404, filed on Nov. 9, 2012.

(51) Int. Cl.
*G02B 5/32* (2006.01)
*H01L 31/052* (2014.01)
(Continued)

(52) U.S. Cl.
CPC .............. *G02B 5/32* (2013.01); *A01G 33/00* (2013.01); *A01H 3/02* (2013.01); *C12M 21/02* (2013.01);
(Continued)

(58) Field of Classification Search
CPC ............ G02B 19/0042; G02B 19/1086; G02B 19/32; A01G 33/00; H01L 31/0549;
(Continued)

(56) References Cited

U.S. PATENT DOCUMENTS 4,204,881 A 5/1980 McGrew
4,328,389 A 5/1982 Stern et al.
(Continued)

FOREIGN PATENT DOCUMENTS

EP 1348145 B1 9/2006
EP 2141748.6 8/2011
WO WO 2003038348 5/2003

OTHER PUBLICATIONS

Bainier et al., "Solar Concentrating Systems Using Holographic Lenses," Solar & Wind Technology, vol. 5, No. 4, 1988, pp. 395-404.
(Continued)

*Primary Examiner* — Matthew T Martin
(74) *Attorney, Agent, or Firm* — Davis Wright Tremaine LLP

(57) ABSTRACT

An apparatus for obtaining energy from a polychromatic energy source that emits radiation in a first and a second wavelength band comprises a reflector or an energy receiver having an aperture therein; and a holographic lens that diffracts and focuses the radiation within the first wavelength band from the energy source through said aperture towards a first energy receiver, and transmits the radiation within the second wavelength band from the energy source to the reflector or energy receiver. If a reflector is used, the reflector reflects the radiation transmitted by the holographic lens towards a second energy receiver.

23 Claims, 4 Drawing Sheets

(51) Int. Cl.
*A01G 33/00* (2006.01)
*G02B 19/00* (2006.01)
*G02B 27/10* (2006.01)
*A01H 3/02* (2006.01)
*C12N 1/12* (2006.01)
*C12N 13/00* (2006.01)
*C12M 1/00* (2006.01)
*H02S 40/22* (2014.01)
*H01L 31/054* (2014.01)
*F24S 23/00* (2018.01)

(52) U.S. Cl.
CPC ............ *C12M 31/06* (2013.01); *C12N 1/12* (2013.01); *C12N 13/00* (2013.01); *F24S 23/00* (2018.05); *G02B 19/0042* (2013.01); *G02B 27/1086* (2013.01); *H01L 31/0549* (2014.12); *H02S 40/22* (2014.12); *Y02E 10/44* (2013.01); *Y02E 10/52* (2013.01); *Y02P 60/12* (2015.11)

(58) Field of Classification Search
CPC .......... C12N 13/00; C12N 1/12; C12M 31/06; F24J 2/06; H02S 40/22; Y02E 10/52
See application file for complete search history.

(56) References Cited

U.S. PATENT DOCUMENTS

| | | | |
|---|---|---|---|
| 4,490,981 A * | 1/1985 | Meckler | F03G 6/001 126/600 |
| 4,700,013 A | 10/1987 | Soule | |
| 6,274,860 B1 | 8/2001 | Rosenberg | |
| 7,077,361 B1 * | 7/2006 | Rabinowitz | B64G 1/44 244/172.8 |
| 7,315,377 B2 | 1/2008 | Holland et al. | |
| 2009/0056698 A1 * | 3/2009 | Johnson | F24J 2/1047 126/569 |
| 2009/0255568 A1 * | 10/2009 | Morgan | F24J 2/062 136/246 |
| 2010/0186818 A1 | 7/2010 | Okorogu et al. | |

OTHER PUBLICATIONS

Fröhlich et al., "Fabrication and Test of Holographic Concentrator for Two Color PV—Operation," SPIE, vol. 2255, Apr. 1994, pp. 812-821.

Castro et al., "Energy Collection Efficiency of Holographic Planar Solar Concentrators," Applied Optics, vol. 49, No. 5, Feb. 10, 2010, pp. 858-870.

Imenes et al., "Spectral Beam Splitting Technology for Increased Conversion Efficiency in Solar Concentrating Systems: A Review," Solar Energy Materials and Solar Cells, 84 (2004) pp. 19-69.

Ludman et al., "The Optimization of a Holographic System for Solar Power Generation," Solar Energy, vol. 60, No. 1, 1997, pp. 1-9.

Segal et al., "Hybrid Concentrated Photovoltaic and Thermal Power Conversion at Different Spectral Bands," Solar Energy, 76 (2004) pp. 561-601.

Shakher et al., "Volume Holographic Lenses and Their Applications in White Light Imaging and Concentration of Solar Energy," Proceedings of SPIE, vol. 4924, 2002, pp. 174-185.

Zhang, "Holographic Spectrum-Splitting Optical Systems for Solar Photovoltaics," Dissertation submitted to Department of Electrical and Computer Engineering, 2013, p. 1-159.

Zhang, et al., "Spectrum-Splitting Photovoltaic System Using Transmission Holographic Lenses," Journal of Photonics for Energy, vol. 3, 2013, pp. 034597-1 thru 034597-12.

* cited by examiner

HOLOGRAPHIC DIFFRACTION-THROUGH-APERTURE SPECTRUM SPLITTING SYSTEM AND METHOD

CROSS-REFERENCE TO RELATED APPLICATION

This application claims priority to and receives the benefit of U.S. Provisional Patent Application No. 61/796,404 filed Nov. 9, 2012, which application is incorporated herein in its entirety by this reference.

This invention was made with government support under Grant No. EEC1041895 and ECCS0925085 awarded by the National Science Foundation. The government has certain rights in the invention.

BACKGROUND OF THE INVENTION

Efficient collection and concentration of radiant energy is useful in a number of applications and is of particular value for devices that convert solar energy to electrical, thermal or biofuel energy. The different types of solar energy conversions have different spectral requirements. Thus, thermal power generation from solar energy is spectrally insensitive, while photosynthesis and photovoltaic (PV) solar cells require specific spectral bands. It is thus possible to split the spectrum of solar energy to maximize use of the solar spectrum for the conversion. In other words, the solar energy is split so that the solar energy in the spectral band for photosynthesis and photovoltaic solar cells are used for conversion by photosynthesis and photoelectric conversion, while the rest of the solar spectrum is directed to thermal conversion.

Dichroic filters have been proposed for performing the function of splitting the solar spectrum. U.S. Pat. No. 7,741,557 discloses one technique using dichroic filters for splitting the solar spectrum. Dichroic filters however are made by individual deposition of hundreds of layers with specified indices of refraction and are quite fragile. This approach requires time and precision and is not economically viable for application to large areas of solar power conversion. Thus, dichroic filters are up to six times as expensive as conventional light filters.

Another material that splits light spectrum is luminescent dye. Luminescent dye can absorb and reflect specific wavelengths of light. However, dyes are plagued with many logistical issues. Among the problems with dyes are reabsorption losses, and inefficient use of the light spectrum. Dyes emit light in all directions and it may be difficult to utilize all of the light emitted by luminescent dyes.

Prisms may also be used for spectrum splitting, but is inefficient because prisms would separate all the bands in the solar spectrum, whereas separation of only one band may be all that is needed.

It is thus desirable to provide a mechanism and method for splitting the energy spectrum that are superior to the above noted techniques.

SUMMARY OF THE INVENTION

One embodiment of the invention is directed towards an apparatus for obtaining energy from a polychromatic energy source that emits radiation in a first and a second wavelength band. The apparatus comprises a reflector having an aperture therein; and a holographic lens that diffracts and focuses the radiation within the first wavelength band from the energy source through said aperture towards a first energy receiver, and transmits the radiation within the second wavelength band from the energy source to the reflector, wherein the reflector reflects the radiation transmitted by the holographic lens towards a second energy receiver.

Another embodiment of the invention is directed towards an apparatus for obtaining energy from a polychromatic energy source that emits radiation in a first and a second wavelength band. The apparatus comprises a first energy receiver having an aperture therein, the first energy receiver suitable for converting or storing energy from radiation within the first wavelength band, and a holographic lens that diffracts and focuses the radiation within the second wavelength band from the energy source through said aperture towards a second energy receiver, and transmits the radiation within the first wavelength band from the energy source to the first energy receiver.

Yet one more embodiment of the invention is directed towards a method for obtaining energy from a polychromatic energy source that emits radiation in a first and a second wavelength band, employing a reflector or a first energy receiver having an aperture therein. The method comprises using a holographic lens to diffract and focus the radiation within the second wavelength band from the energy source through the aperture towards a second energy receiver, and transmitting the radiation within the first wavelength band through the holographic lens from the energy source to the first energy receiver or the reflector.

All patents, patent applications, articles, books, specifications, other publications, documents and things referenced herein are hereby incorporated herein by this reference in their entirety for all purposes. To the extent of any inconsistency or conflict in the definition or use of a term between any of the incorporated publications, documents or things and the text of the present document, the definition or use of the term in the present document shall prevail.

BRIEF DESCRIPTION OF THE DRAWINGS

For simplicity in description, identical components are labeled by the same numerals in this Application.

DETAILED DESCRIPTION

Solar panel, or photovoltaic (PV), technology converts sunlight directly into electricity through the photoelectric effect. Solar thermal electric energy generation concentrates the light from the sun to create heat, and that heat is used to run a heat engine, which turns a generator to make electricity. Alternatively, the heat engine may also be used to heat a gas, or turn a liquid such as water into a gas such as steam, to drive a motor. The energy receivers used in the above mentioned thermal generation from sun light or other types of radiation sources are referred to herein as thermal receivers.

Another mechanism for capturing solar energy is by means of photosynthesis, such as by means of algae, corn, or any other type of plants that uses light from the sun or other radiation sources to create any type of fuel that may be used for energy generation.

All of the above mentioned devices or plants that capture solar energy or energy from other types of radiation sources are referred to herein as energy receivers.

A hologram is an interference pattern recorded in photosensitive material. Upon illumination, the hologram transmits light of a specific wavelength range the direction of a signal beam. In the case of a holographic lens, the signal beam is a converging wavefront.

A feature of the invention is the idea that while solar photovoltaic cells or thermal receivers may be used as the primary energy receivers to capture and use solar energy, wasted portions of light are directed towards secondary energy receivers such as algae. Thus, in one embodiment of this invention, modified holographic lenses are added to a solar collection array. The center of each primary energy receiver, such as a photovoltaic panel or collection mirror in an array of such receivers, will have an open aperture located at or near the focal point of the holographic lens. Each of the holographic lenses diffracts an appropriate wavelength range from the incident radiation toward a spectrally-selective secondary energy receiver located at or beyond an aperture at the center of the primary solar receiver. The remaining spectrum transmits through the holographic lens unaffected, reaching the primary energy receiver such as the solar array.

Figures 1, 2:
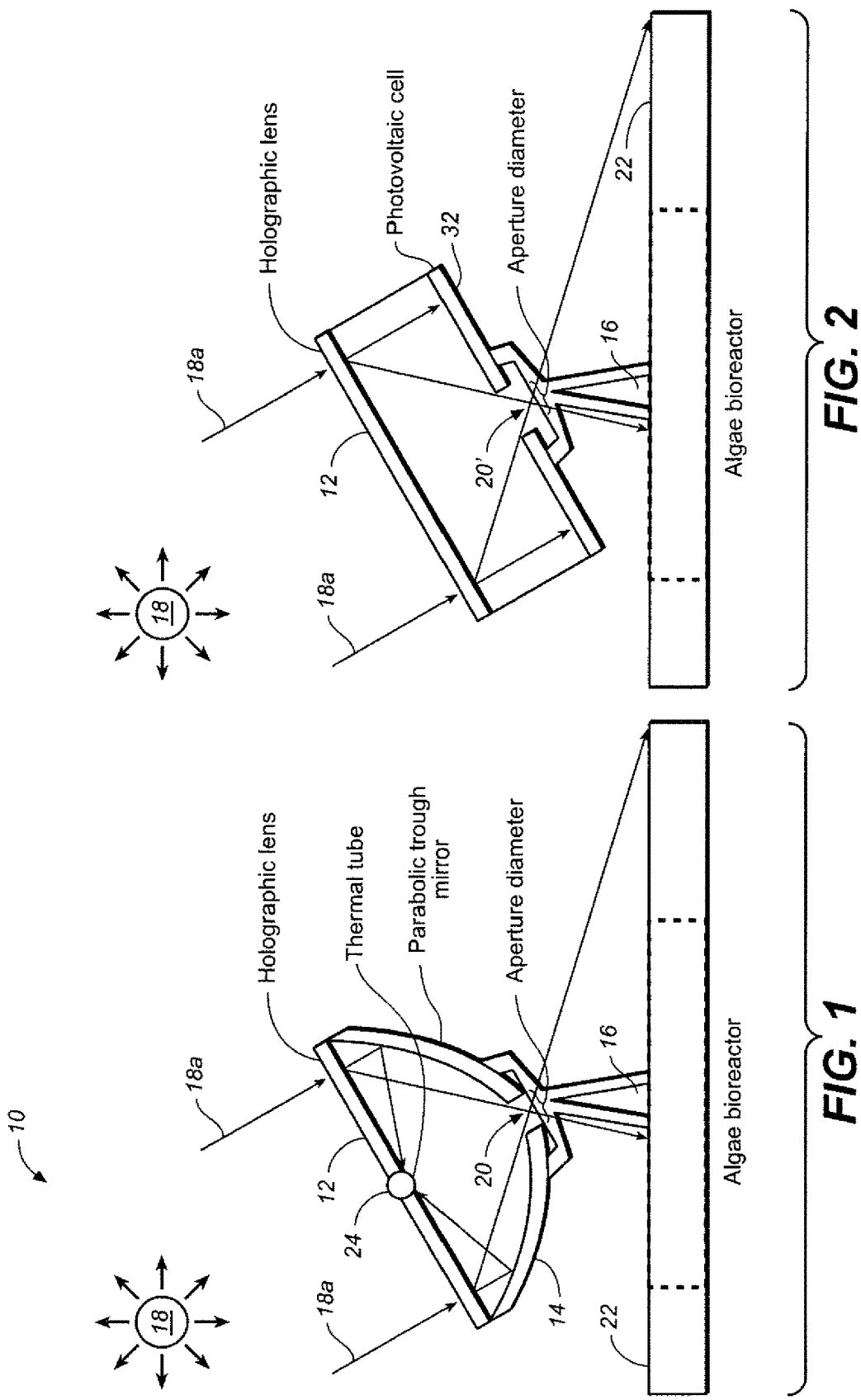
FIG. 1 is a schematic diagram of a holographic diffraction-through-aperture spectrum splitting system illustrating one embodiment of the invention.
FIG. 2 is a schematic diagram of a holographic diffraction-through-aperture spectrum splitting system illustrating another embodiment of the invention.

Two specific realizations of the invention include a parabolic thermal mirror array (which may be rotationally symmetric or an extended trough) as shown in FIG. 1 and a flat-panel photovoltaic array, as shown in FIG. 2. In both cases, the holographic lens is mounted one focal length from the center of the solar collector and tracks the sun along at least one axis.

FIG. 1 is a schematic diagram of a holographic diffraction-through-aperture spectrum splitting system illustrating one embodiment of the invention. As shown in FIG. 1, a spectrum splitting system 10 comprises a holographic lens 12 connected to and supported by a curved mirror 14, such as a parabolic trough mirror, which in turn is connected to and supported by a stand 16. The holographic lens 12 is situated or located between the mirror 14 and the sun 18. The mirror 14 has an aperture 20 therein. The holographic lens 12 diffracts and focuses in an appropriate wavelength range from the incident radiation 18a from the sun 18 toward a spectrally-selective secondary energy receiver 22 located at or beyond aperture 20 at the center of the mirror. The focal point of the holographic lens 12 is preferably at or near aperture 20. The holographic lens 12 transmits radiation that is not diffracted in the remainder of the solar wavelength range towards a primary solar receiver 24, which in this instance is a thermal receiver, such as a thermal tube. The spectrally-selective secondary energy receiver 22 may be algae, corn, or any other type of photosensitive plants that capture energy from radiation sources by means of photosynthesis.

FIG. 2 is a schematic diagram of a holographic diffraction-through-aperture spectrum splitting system illustrating another embodiment of the invention. The only difference between the embodiments of FIGS. 1 and 2 is that, mirror 14 and thermal tube 24 are replaced by photovoltaic cell 32 located between the holographic lens 12 and the secondary energy receiver 22, so that the radiation that is not diffracted by the holographic lens 12 in the remainder of the solar wavelength range is transmitted to the photovoltaic cell 32 as the primary energy receiver. Photovoltaic cell 32 is supported by stand 16. Photovoltaic cell 32 also defines an aperture 20' therein. The focal point of holographic lens 12 is at or near the aperture 20'. The holographic lens 12 diffracts and focuses in an appropriate wavelength range from the incident radiation 18a from the sun 18 toward spectrally-selective secondary energy receiver 22 located at or beyond aperture 20 at the center of the photovoltaic cell 32.

The secondary energy receiver 22, such as algae or corn, may have a limited useful wavelength range for photosynthesis, such as wavelengths in the range of 400-700 nm. For this reason, it is preferably to use holographic lens 12 to diffract radiation in this wavelength range towards the secondary energy receiver 22, and to transmit the radiation in the remainder of the solar spectrum to the primary energy receiver 32 or 24.

Each of the systems in FIGS. 1 and 2 may be deployed in the form of an array comprising many of these systems, with each of them tracking the sun 18 in the course of the day.

Modifications to the Basic Holographic Lens 20

Figure 3:
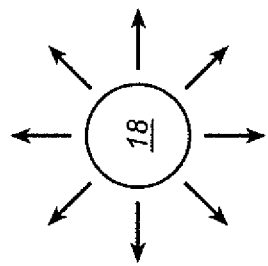
FIGS. 3 and 4 are schematic diagrams of a holographic diffraction-through-aperture spectrum splitting system illustrating yet more embodiments of the invention.
Figure 3:
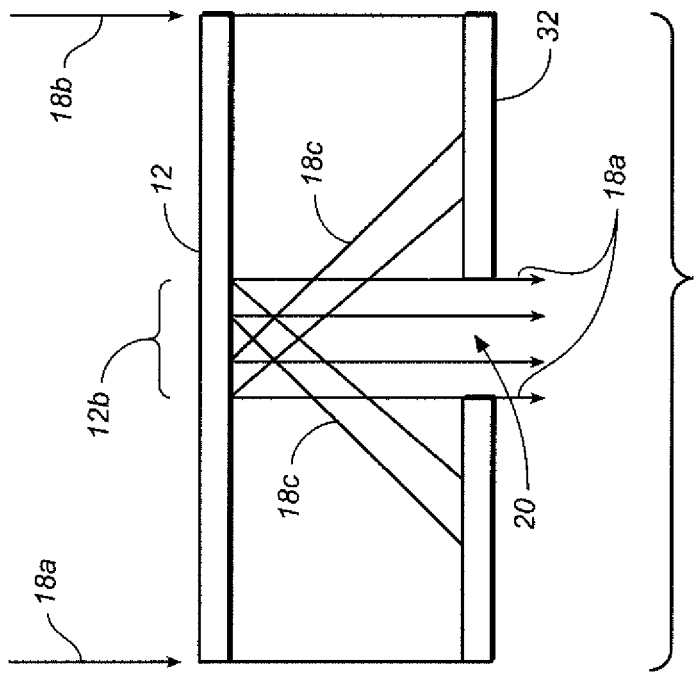

In the case of the thermal collection mirror array as in FIGS. 1 and 3, the holographic lens is modified in the sense that it is broken into two symmetric pieces on either side of a thermal receiver tube.

Figure 4:
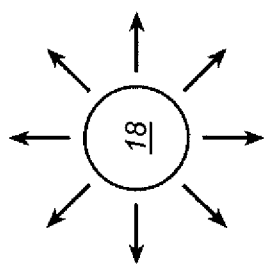
Figure 4:
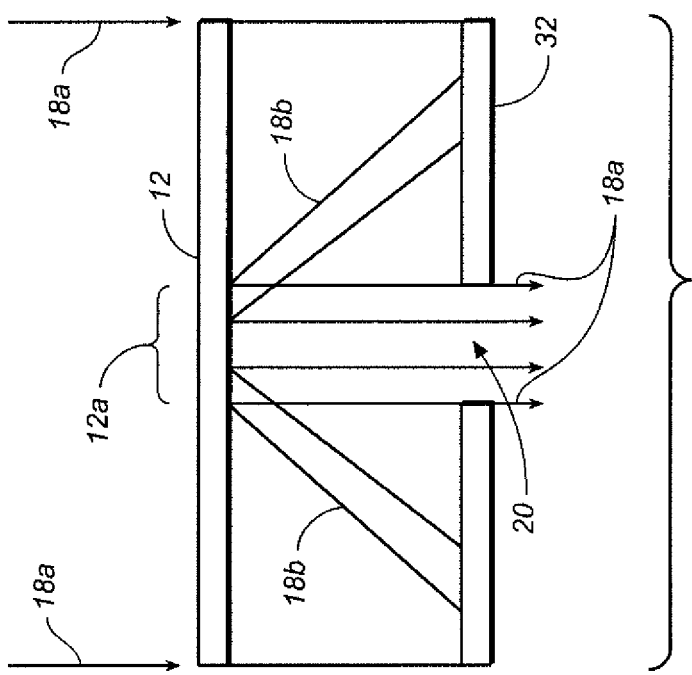

In the case of a photovoltaic collection array as in FIG. 2, the holographic lens 12 is modified in a more significant way. Because the secondary energy receiver 22 requires a more narrow wavelength band (e.g. 400-700 nm) within that of the primary energy receiver 32, the region of the holographic lens that is directly above the aperture should be modified. In these regions, a basic holographic lens would have diffracted a broad bandwidth of light toward the aperture (because the diffracted angle is small). Additionally, the spectrum that did not get diffracted would also pass through the aperture rather than reaching the broad-bandwidth collector. For the purpose of the spectrum-splitting application, regions of the holographic lens directly above the aperture and located between the sun and the aperture should instead diffract light that is beyond the secondary energy receiver's range of spectral sensitivity or selectivity away from the focal point and toward the photovoltaic panel instead. This will increase the efficiency of converting solar energy, since the light that is beyond the secondary energy receiver's range of spectral sensitivity is now directed towards the photovoltaic panel instead of the secondary energy receiver and will not be wasted. This is illustrated in FIGS. 3 and 4. As shown in these figures, radiation within the secondary energy receiver's range of spectral sensitivity is transmitted by the modified regions or portions 12a and 12b of the holographic lens 12 above the aperture 20, but radiation not within the secondary energy receiver's range of spectral sensitivity is diffracted along paths 18b and 18c away from the aperture 20 and towards the photovoltaic primary energy receiver 32.

In FIG. 3, modified region or portion 12a diffracts light on the left side of the portion to the left side of the PV cell 32, and diffracts light on the right side of the portion to the right side of the PV cell 32. In other words, the diffracted light beams 18b split. Unaffected part of the solar beam 18a by portion 12a is transmitted to the secondary energy receiver (not shown).

In FIG. 4, modified region or portion 12b diffracts light on the left side of the portion to the right side of PV cell 32, and diffracts light on the right side of the portion to the left side of PV cell 32. In other words, the diffracted light beams 18c cross. Unaffected part of the solar beam 18a by portion 12b is transmitted to the secondary energy receiver (not shown).

Optimization of System

To model this hologram, the holographic lens is broken into small sections, which may be approximated as planar volume transmission holograms. The diffraction efficiency of each section can be calculated using Kogelnik Approximate Coupled Wave Analysis (ACWA). The diffracted angle for every wavelength in each section of the lens is found, and ray-tracing is used to determine the final destination.

Performance is based on a spectral optical efficiency, is defined as the fraction of incident light of a particular wavelength reaching each receiver. Incident light falls into three categories after interacting with the holographic lens:

1) Not diffracted: light is collected in the thermal or PV receiver.
2) Diffracted into aperture: light is collected in the secondary energy receiver.
3) Diffracted outside of aperture: light either misses the thermal receiver (optical loss), or is collected by the PV receiver.

Figure 5:
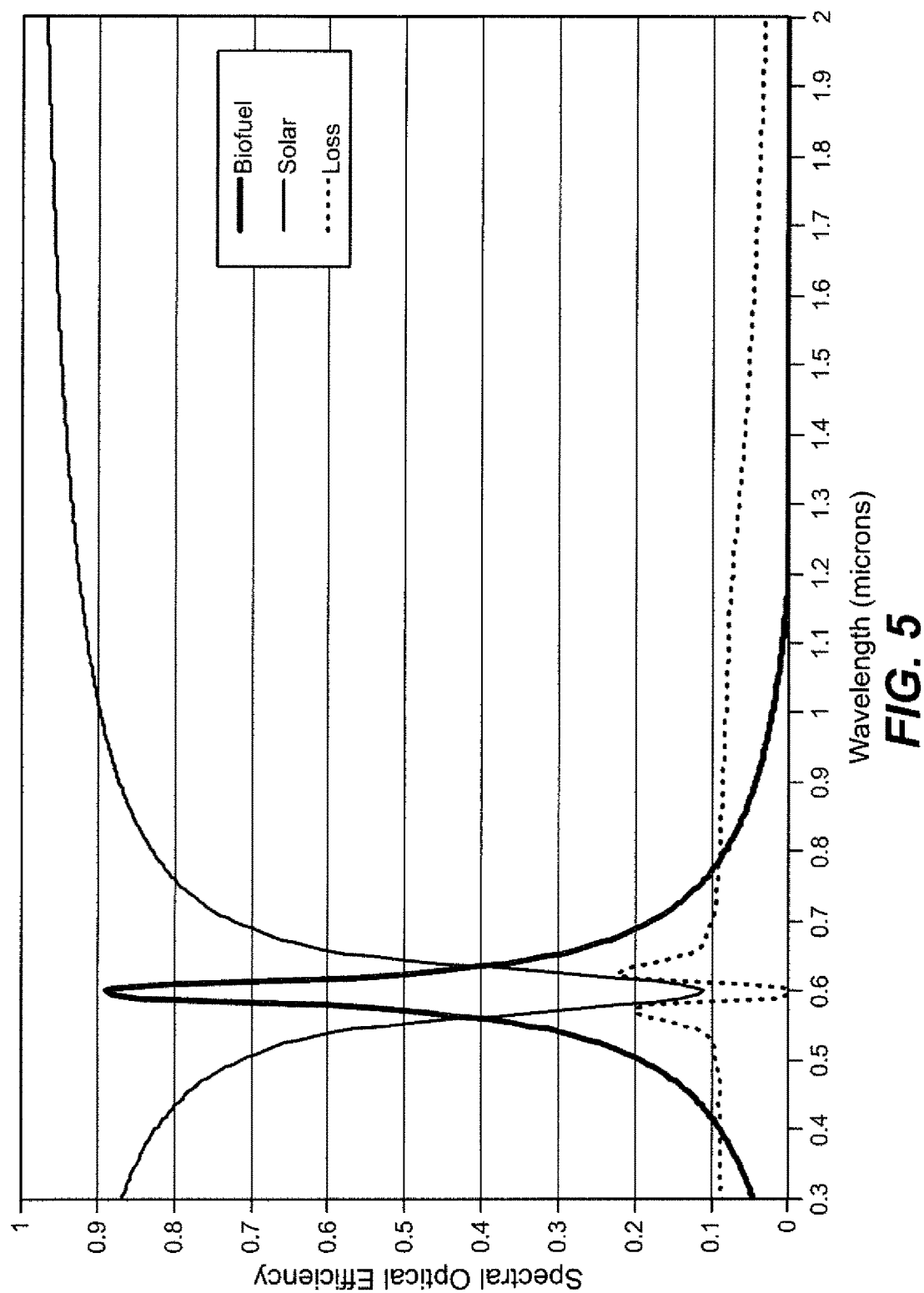
FIG. 5 is a graphical plot of spectral optical efficiency in each of the categories of biofuel, solar and loss.

A typical plot of spectral optical efficiency in each category is shown in FIG. 5.

Figure 6:
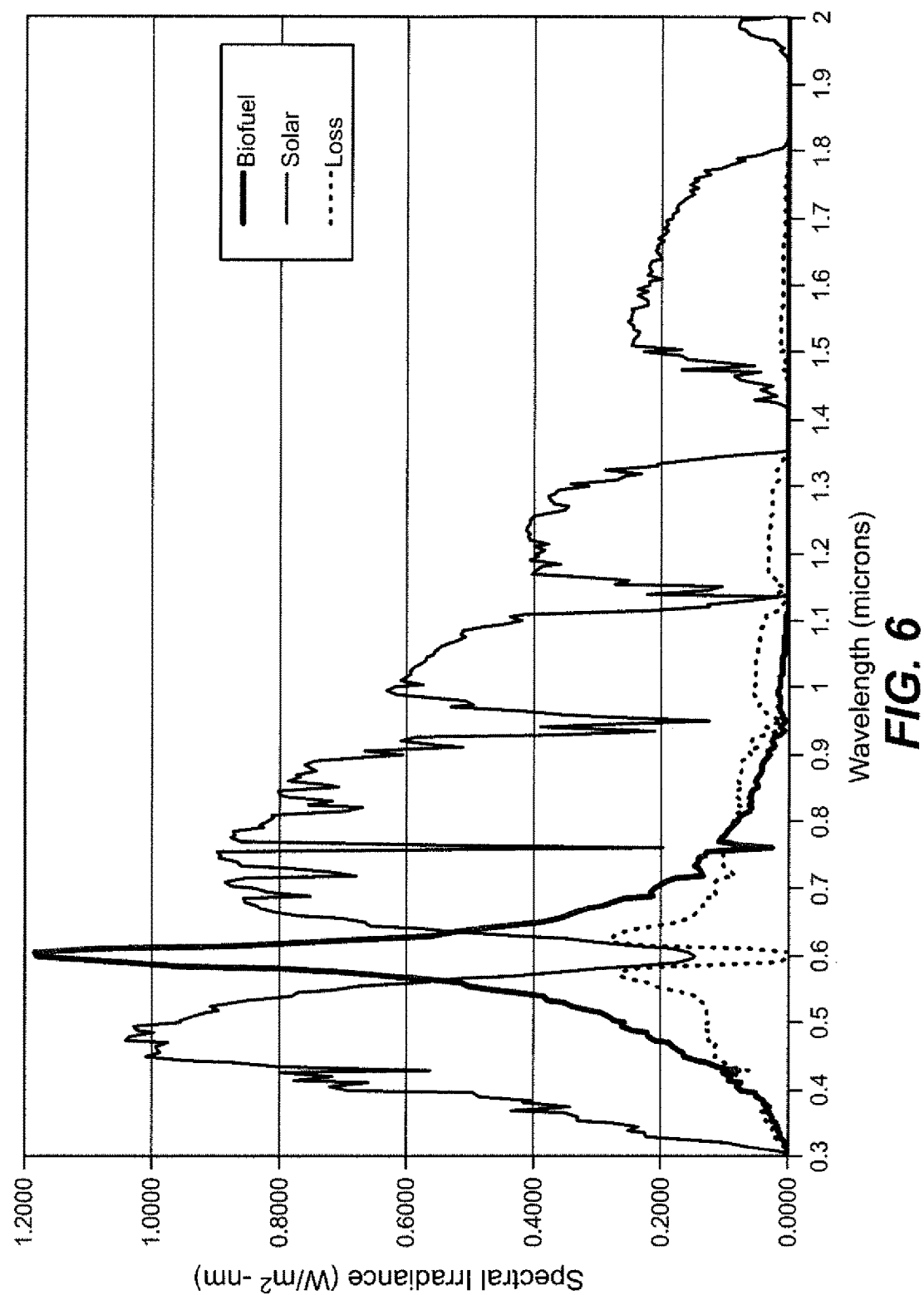
FIG. 6 is a graphical plot of the spectral irradiance curves corresponding to FIG. 5. An AM 1.5 solar spectrum is used.

The spectral irradiance reaching each receiver equals incident spectral irradiance multiplied by spectral optical efficiency. Using an AM 1.5 solar spectrum, the spectral irradiance curves corresponding to FIG. 3 are shown in FIG. 6.

Variables that may be controlled in the design to optimize performance include holographic lens (HL) diameter and focal length, hologram film thickness, and aperture diameter. Varying aperture width or film thickness will affect the bandwidth of light reaching the secondary energy receiver. Varying focal length involves a tradeoff between system compactness and polarization-based loss in holographic diffraction. A realistic range of values for each value is shown in the following table. These values are chosen for the particular application of a spectrum-splitting solar array.

| Parameter | Range |
| --- | --- |
| HL Diameter | 20 cm-2 m |
| HL Focal Length | 5 cm-3 m |
| Aperture Diameter | 1 cm-15 cm |
| Film Thickness | 1-100 μm |

System Design Considerations

Optimization will ultimately depend on the goal of the hybrid system. Possible objectives include, 1. Maximize solar-to-electric power conversion by using a thermal mirror array with a photovoltaic cell as the secondary energy receiver.
2. Create a specific ratio of PV and thermal energy production to provide stability in an intermittent climate.
3. Produce a specific minimum biofuel yield, while devoting remaining solar energy to electricity generation in photovoltaic panels.

By choosing appropriate holographic lens design modifications and varying the system parameters listed above, the spectral optical efficiency curves may be modified to achieve the design goal.

As explained above, the splitting of the solar spectrum allows the solar energy not otherwise used for PV and thermal energy production to be used productively by directing it to photosensitive plants such as algae and corn. Design parameters may be controlled to achieve a ratio between biofuel production on one hand and PV and thermal energy production on the other. Because the diffraction efficiency of the holographic lens can always be reduced, and because the aperture size can be made very small, the lower end of the energy distribution range would be 0:100 (where 0% of solar energy reaches the algae and 100% reaches the PV or thermal collector) or a ratio close to it, such as 1:99. On the other end of the range, a realistic ratio is 62:38 (62% reaches algae, 38% reaches PV or thermal).

One of the applications for embodiments of the invention is to use the holographic lens and mirror/PV aperture combination to split light in such a way that relevant portions are deflected onto photosynthetic plants. These plants can then be used as fuel. This application leverages algae as a potential option, while another choice could be corn. Corn is the leading feedstock into the ethanol fuel industry which could replace up to 30% of United States petroleum demand by 2030 (Department of Energy). Selecting corn or algae should be possible as both organisms are photosynthetic, and the same lens can be used to diffract the same band of light. Effectively, embodiments of this invention enable the optimization of the energy derived from sunlight to power both photovoltaic cells and allow algae or corn to flourish.

Another option would be to forgo the plant route and instead use different types of photovoltaic cells to increase energy efficiency. It has been demonstrated that different photovoltaic cells can have different spectral sensitivities. Therefore, another embodiment of the invention is to use a holographic lens that can divide light such that each cell is exposed only to light that it is most sensitive to. In this embodiment, the secondary energy receiver 22 in each of FIGS. 1-3 would be PV solar cells instead of algae. Of course, the secondary energy receiver 22 in each of FIGS. 1-3 can also be thermal energy receivers instead of algae or PV solar cells. But given that photosynthesis and PV conversion are more selective in their sensitivity to the spectral range than thermal energy receivers, it is preferable to deploy either photosensitive plants or PV cells as the secondary energy receiver 22.

Instead of PV cell 32 in FIG. 2, a thermal energy receiver may be used in place of the PV cell 32. Instead of reflecting radiation towards a thermal energy receiver as in FIG. 1, the mirror 14 may reflect radiation towards PV cells instead. Such and other variations are within the scope of the invention.

While the invention has been described above by reference to various embodiments, it will be understood that changes and modifications may be made without departing from the scope of the invention, which is to be defined only by the appended claims and their equivalents. While the embodiments described above refer to the sun as the energy source, these embodiments are equally applicable where the energy source is not the sun but also a polychromatic energy source.

We claim:

1. A diffraction-through-aperture spectrum splitting apparatus for obtaining energy from a polychromatic energy source that emits radiation in a first and a second wavelength band, comprising:

a reflector having an open aperture therethrough;
a first and a second energy receiver, wherein the first energy receiver includes photosensitive plants or algae, and the second energy receiver includes photovoltaic cells or a thermal receiver; and
a holographic lens configured to split the polychromatic energy into the first and the second wavelength bands such that it diffracts and focuses the radiation within the first wavelength band from the energy source through and beyond said open aperture for capture beyond said open aperture by the first energy receiver positioned beyond the open aperture, and transmits the radiation within the second wavelength band from the energy source to the reflector, wherein the reflector is configured to reflect the radiation transmitted by the holographic lens towards the second energy receiver, wherein the open aperture is positioned between the first and the second energy receivers.

2. The apparatus of claim 1, wherein said reflector includes a mirror.

3. The apparatus of claim 2, wherein said mirror has a curved shape, said mirror focusing the radiation transmitted by the holographic lens towards said second energy receiver.

4. The apparatus of claim 1, wherein said reflector includes at least one reflection hologram.

5. The apparatus of claim 1, wherein a focal point of the holographic lens is substantially at or near the open aperture of the reflector.

6. The apparatus of claim 1, wherein the polychromatic energy source is located above the holographic lens and the reflector, and a portion of the holographic lens located above the open aperture and between the energy source and the open aperture diffracts radiation of selected wavelengths away from the open aperture so that radiation of the selected wavelengths reaches the second energy receiver instead of the first energy receiver, and wherein said selected wavelengths are beyond spectral sensitivity range of the first energy receiver.

7. The apparatus of claim 1, wherein the holographic lens has a diameter in a range of about 20 cm to 2 m, a focal length in a range of about 5 cm to 3 m, and a film thickness of a hologram in the holographic lens is in a range of about 1 to 100 microns.

8. The apparatus of claim 1, wherein the open aperture has a diameter in a range of about 1 cm to 15 cm.

9. The apparatus of claim 1, wherein, the first energy receiver further comprises photovoltaic cells.

10. A diffraction-through-aperture spectrum splitting apparatus for obtaining energy from a polychromatic energy source that emits radiation in a first and a second wavelength band, comprising:
a first energy receiver having an open aperture therethrough, the first energy receiver suitable for converting or storing energy from radiation within the first wavelength band; and
a holographic lens configured to split the first and the second wavelength bands such that it diffracts and focuses the radiation within the second wavelength band from the energy source through and beyond the open aperture for capture beyond the open aperture by a second energy receiver positioned beyond the open aperture, and transmits the radiation within the first wavelength band from the energy source to the first energy receiver, wherein the open aperture is positioned between the first and the second energy receivers, wherein the first energy receiver includes photovoltaic cells or a thermal receiver, and the second energy receiver includes photosensitive plants or algae.

11. The apparatus of claim 10, wherein a focal point of the holographic lens is substantially at or near the open aperture.

12. The apparatus of claim 10, wherein the polychromatic energy source is located above the holographic lens and the first energy receiver, and a portion of the holographic lens located above the open aperture and between the energy source and the open aperture diffracts radiation of selected wavelengths away from the open aperture so that radiation of the selected wavelengths reaches the first energy receiver instead of the second energy receiver, and wherein said selected wavelengths are beyond spectral sensitivity range of the second energy receiver.

13. The apparatus of claim 10, wherein the holographic lens has a diameter in a range of about 20 cm to 2 m, a focal length in a range of about 5 cm to 3 m, and a film thickness of a hologram in the holographic lens is in a range of about 1 to 100 microns.

14. The apparatus of claim 10, wherein the aperture has a diameter in a range of about 1 cm to 15 cm.

15. The apparatus of claim 10, wherein the second energy receiver further comprises photovoltaic cells.

16. The apparatus of claim 10, wherein the first energy receiver includes photovoltaic cells or a thermal receiver, and the second energy receiver includes photosensitive plants.

17. The apparatus of claim 10, wherein a ratio between energy diffracted and focused by the holographic lens to the second energy receiver to the energy transmitted by the holographic lens to the first energy receiver is in a range of about 1:99 to about 62:38.

18. A diffraction-through-aperture spectrum splitting method for obtaining energy from a polychromatic energy source that emits radiation in a first and a second wavelength band, employing a reflector or a first energy receiver, in each case having an open aperture therethrough, comprising:
diffracting and focusing, using a holographic lens configured to split the first and the second wavelength bands, the radiation within the second wavelength band from the energy source through and beyond the open aperture for capture beyond the open aperture by a second energy receiver positioned beyond the reflector open aperture or beyond the first energy receiver open aperture, wherein the second energy receiver includes photosensitive plants or algae; and
transmitting the radiation within the first wavelength band through the holographic lens from the energy source to the first energy receiver or to the reflector, in each case wherein the open aperture is positioned between the first and the second energy receivers, or wherein the open aperture is positioned between the reflector and the second energy receiver.

19. The method of claim 18, wherein the radiation transmitted to the reflector is reflected by the reflector towards a third energy receiver.

20. The method of claim 18, wherein the radiation within the second wavelength band from the energy source is diffracted and focused through and beyond the open aperture for capture beyond the open aperture by photosensitive plants.

21. The method of claim 18, wherein the radiation within the second wavelength band from the energy source is diffracted and focused through and beyond the open aperture for capture beyond the open aperture by algae or corn.

22. The method of claim 18, wherein the radiation within the first wavelength band from the energy source is reflected by the reflector towards a thermal energy receiver or photovoltaic solar cells.

23. The method of claim 18, wherein the radiation within the first wavelength band from the energy source is transmitted to a thermal energy receiver or photovoltaic solar cells.

* * * * *